United States Patent [19]

Tuttle et al.

[11] 3,987,200

[45] Oct. 19, 1976

[54] METHOD FOR INCREASING CARDIAC CONTRACTILITY

[75] Inventors: Ronald R. Tuttle; Jack Mills, both of Indianapolis, Ind.

[73] Assignee: Eli Lilly and Company, Indianapolis, Ind.

[22] Filed: Jan. 15, 1975

[21] Appl. No.: 541,179

Related U.S. Application Data

[62] Division of Ser. No. 243,466, April 12, 1972, abandoned.

[52] U.S. Cl. ................................................ 424/330
[51] Int. Cl.² ........................................ A61K 31/135
[58] Field of Search ..................................... 424/330

[56] References Cited

UNITED STATES PATENTS 2,276,619   3/1942   Kulz ................................. 260/570.8

Primary Examiner—Sam Rosen
Attorney, Agent, or Firm—William B. Scanlon; Everet F. Smith

[57] ABSTRACT

N-Mono or dihydroxyphenylalkyl dopamine derivatives and salts thereof are inotropic agents useful in a method for treatment of acutely depressed cardiac insufficiency.

8 Claims, No Drawings

METHOD FOR INCREASING CARDIAC CONTRACTILITY

This is a division of application Ser. No. 243,466, filed Apr. 12, 1972 now abandoned.

BACKGROUND OF THE INVENTION

This invention relates to certain novel derivatives of dopamine and to a method for the treatment of acutely depressed cardiac contractility employing such derivatives. In particular, this invention relates to 3,4-dihydroxy-N-(3-, and 4-monohydroxy-, or 3,4-dihydroxyphenylpropyl or phenylethyl)-phenethyl amines, the racemic mixtures, the optical antipodes, and the pharmaceutically acceptable acid addition salts thereof formed with mineral acids.

The clinical syndrome shock arises from a variety of causes; however, depression of the heart's contractility is frequently a contributing factor. Shock due to inadequate cardiac contractility is referred to as cardiogenic shock and is a leading cause of death. An agent for the treatment of cardiogenic shock should have a powerful inotropic effect so that it can fully reverse the cardiac contractile depression.

The sympathomimetic agents norepinephrine and isoproterenol, currently used to restore contractility in cardiogenic shock, have side effects which are life threatening.

Norepinephrine causes a vasoconstriction that can reduce blood flow to vital organs and excessively elevate aortic pressure, thereby increasing the heart's work and oxygen demand. In contrast, isoproterenol causes an excessive vasodilation in skeletal muscle diverting blood flow to that region at the expense of flow to the vital organs. Both norepinephrine and isoproterenol may induce fatal arrhythmias.

Another sympathomimetic agent, dopamine, (3,4-dihydroxyphenylethylamine) has also been used clinically for the treatment of acutely depressed cardiac contractility and shock. This drug, however, causes the release of endogenous norepinephrine and exposes the patient to life threatening cardiac arrhythmias.

Surprisingly, we have found that N substitution of dopamine or α-methyldopamine by a mono- or dihydroxyphenylalkyl group, provides compounds that are direct acting β-agonists, i.e., compounds which increase cardiac contractility without releasing norepinephrine. Further, at doses that produce an equivalent increase in contractility the threat of arrhythmia is significantly less than with norepinephrine, isoproterenol or dopamine.

The cardiac stimulant amines of the present invention exert a positive inotropic effect on heart muscle without a significant increase in heart rate. At equivalent doses, the increase in heart rate is less than that produced with isoproterenol.

SUMMARY OF THE INVENTION

This invention provides a method for the treatment of acutely depressed cardiac contractility which comprises the administration of an N-monohydroxyphenyl- or dihydroxyphenylalkyl substituted 3,4-dihydroxyphenethylamine or 3,4-dihydroxyphenyl-iso-propylamine represented by the following generalized formula

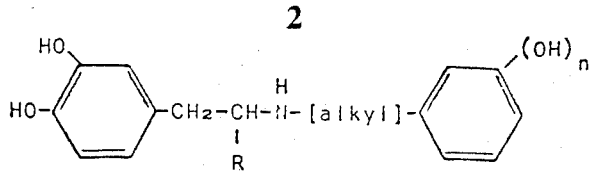

wherein alkyl can be

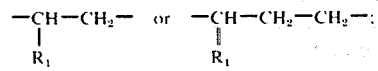

$n$ is 1 or 2; and R and $R_1$ can be hydrogen or methyl.

Certain of the compounds represented above are asymmetric and can be resolved into their optically active antipodes as for example by resolution with dibenzoyl-d- or -l- tartaric acid.

According to the present invention, a compound represented by the above formula in the form of a pharmaceutically acceptable salt, for example the hydrochloride salt, is administered at a rate between about 0.5 and 10 mcg./kg./min. by intravenous infusion to a patient suffering from acutely depressed cardiac contractility. The compounds of the above formula thus administered exert a positive inotropic affect without inducing arrhythmia and with minimal blood pressure effects.

The compounds employed in the method of the invention are prepared with the corresponding methoxy ether derivatives by reacting the methyl ether compounds with 48% hydrobromic acid. The methyl ether precursors are prepared by a variety of synthetic methods. For example, compounds of the above formula wherein R is methyl are prepared by the reductive alkylation of a mono or dimethoxyphenylethylamine or a mono or dimethoxyphenylpropylamine with dimethoxyphenylacetone. Compounds wherein $R_1$ is methyl are prepared by the reductive alkylation of 3,4-dimethoxyphenylethylamine with a mono or dimethoxylated phenylbutan-3-one or a mono or dimethoxylated phenylacetone. Alternatively the methyl ether derivatives of the compounds of the above formula wherein $R_1$ is hydrogen or methyl are prepared by the condensation of 3,4-dimethoxyphenylacetic acid with a mono or dimethoxylated phenylethylamine or phenylpropylamine or with a mono or dimethoxylated phenyl-2-aminopropane or a methoxylated phenyl-3-aminobutane. The amide condensation product of the acid and amine is then reduced with borane to provide the intermediate methoxylated secondary amine.

The methoxy secondary amine precursors prepared by the above procedures are reacted with 48% hydrobromic acid to provide the phenolic secondary amines of the invention.

DETAILED DESCRIPTION OF THE INVENTION

The novel method provided by this invention for the treatment of acutely depressed cardiac contractility comprises the intravenous infusion at a rate of between about 0.5 to 10 mcg./kg. of body weight per minute of a compound represented by the following Formula I.

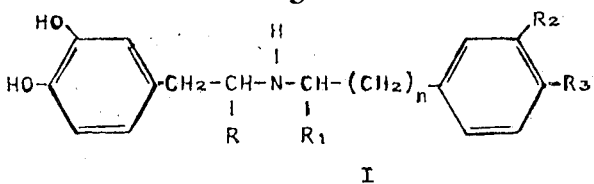

I wherein

R and R₁ are hydrogen or methyl;

R₂ and R₃ are hydrogen or hydroxy, at least one of R₂ and R₃ being hydroxy;

n is 1 or 2;

subject to the limitation that when n is 2, R₂ is hydrogen and R₃ is hydroxy, one of R or R₁ is hydrogen and the other is methyl; and the pharmaceutically acceptable acid addition salts thereof with mineral acids.

The compounds represented by the Formula I when administered according to the present method exert a positive inotropic effect on the heart without the risk of inducing arrhythmia. They increase the contractile force of the heart muscle without increasing heart rate as demonstrated by a high ratio of contractile force to heart rate (CF/HR ratio). In addition, the compounds of Formula I do not restrict blood flow to vital organs, nor do they have an effect on the central nervous system. They are strong β-agonists acting directly on the heart muscle with an immediate onset of action and they are rapidly inactivated. The compounds of the invention act directly on cardiac muscle. That is, they do not rely on the release of norepinephrine for their activity.

The foregoing properties and the inotropic specificity of the compounds of the invention make possible the precise regulation of cardiac contractility by careful adjustment of the rate of intravenous infusion.

Certain of the compounds of the above formula are especially useful in the present method in that they exhibit relatively little hypotensive activity. These preferred compounds are represented by the following formula.

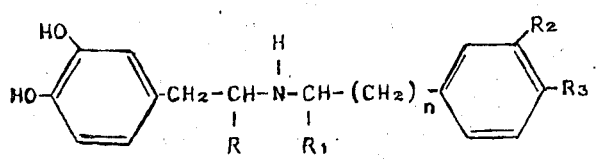

wherein

R and R₁ are hydrogen or methyl;

R₂ and R₃ are hydrogen or hydroxy, at least one of R₂ or R₃ being hydroxy;

n is 1 or 2;

subject to the limitation that when n is 2, R₂ is hydrogen and R₃ is hydroxy, one of R or R₁ is hydrogen and the other is methyl; with the further limitations that when n is 2 and R₂ and R₃ are both hydroxy, then R₁ is hydrogen, and when n is 1, R₂ is hydrogen and R₃ is hydroxy, then R and R₁ are both hydrogen; and the pharmaceutically acceptable acid addition salts with mineral acids.

Illustrative of the compounds which can be employed in the present method are the following:

3,4-dihydroxy-N-[2-(4-hydroxyphenyl)ethyl]-β-phenethylamine, 3,4-dihydroxy-N-[2-(3-hydroxyphenyl)ethyl]-β-phenethylamine, 3,4-dihydroxy-N-[2-(3,4-dihydroxyphenyl)ethyl]-β-phenethylamine, 3,4-dihydroxy-N-[2-(3,4-dihydroxyphenyl)propyl]-β-phenethylamine, 3,4-dihydroxy-N-[2-(3-hydroxyphenyl)-1-methylethyl]-α-methyl-β-phenethylamine, 3,4-dihydroxy-N-[3-(4-hydroxyphenyl)-1-methyl-n-propyl]-β-phenethylamine, 3,4-dihydroxy-N-[3-(4-hydroxyphenyl)-n-propyl]-α-methyl-β-phenethylamine, 3,4-dihydroxy-N-[3-(3-hydroxyphenyl)-n-propyl]-α-methyl-β-phenethylamine, and the pharmaceutically acceptable acid addition salts thereof formed with mineral acids.

The compounds represented by the Formula I wherein either R or R₁ is methyl are asymmetric and can be resolved into optical antipodes as described hereinafter. It is well known that when an asymmetric center exists in a sympathomimetic drug the resolution of the racemic mixture may provide optical isomers with differing pharmacological properties.

Certain of the hydroxylated secondary amines, which are employed in the present method are novel compounds and are represented by the following Formula II,

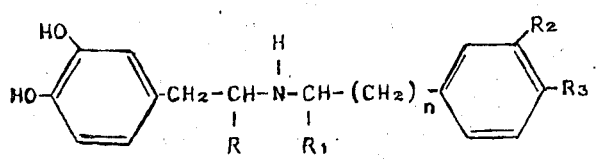

II wherein

R and R₁ are hydrogen or methyl, at least one of R or R₁ being hydrogen;

R₂ and R₃ are hydrogen or hydroxy, at least one of R₂ or R₃ being hydroxy;

n is 1 or 2; and when n is 1 and R₂ and R₃ are both hydroxy, then either R or R₁ is methyl; and the pharmaceutically acceptable acid addition salts thereof with mineral acids.

Preferred compounds of the present invention are 3,4-dihydroxy-N-[3-(4-hydroxyphenyl)-1-methyl-n-propyl]-β-phenethylamine, 3,4-dihydroxy-N-[3-(4-hydroxyphenyl)-n-propyl]-α-methyl-β-phenethylamine, the racemic mixtures, the optical antipodes and the pharmaceutically acceptable acid addition salts thereof formed with mineral acids.

The phenolic amines of the present invention are prepared by reacting the corresponding methyl ether derivative with 48 percent hydrobromic acid. The methyl ether precursors are prepared by a variety of methods. The compounds of the above formulae, where R is methyl and R₁ is hydrogen are prepared by the reductive alkylation of a methoxylated phenylethyl amine or a methoxylated phenylpropyl amine with 3,4-dimethoxyphenylacetone. The reductive alkylation is carried out by dissolving equivalent amounts of the amine and ketone in a suitable solvent, for example, ethanol, methanol or ethyl acetate, and hydrogenating at a hydrogen pressure of from about 25 to 250 psi. in the presence of a hydrogenation catalyst, for example, 5 percent palladium on carbon or Raney nickel. The reductive alkylation can be carried out conveniently at or about room temperature when 5 percent palladium on carbon is the catalyst, or at elevated temperatures of up to 150° C. if Raney nickel is employed as the catalyst. The amount of the catalyst employed in the reaction is not critical and, generally, between about 5 percent and 20 percent of the weight of the amine employed is a convenient amount. The reduction is discontinued when an equivalent of hydrogen has been absorbed. The catalyst is filtered and the filtrate is concentrated by evaporation. The concentrate is then dissolved in ether and the ethereal solution is saturated with anhydrous hydrogen chloride to precipitate the methoxylated secondary amine reaction product as the hydrochloride salt.

According to a second procedure for the preparation of compounds wherein R is methyl and $R_1$ is hydrogen, 3,4-dimethoxyphenylacetone is reacted with a methoxylated phenethylamine or a methoxylated phenylpropylamine in the presence of p-toluenesulfonic acid to form the imine. The imine is thereafter reduced to the secondary amine. According to this method, the amine and the ketone are dissolved in equal molar amounts in toluene or benzene, and a small amount of p-toluenesulfonic acid is added. The solution is then heated at the reflux temperature while the water of reaction is collected in a Dean-Stark water trap. The condensation results in the formation of the imine in about 4 hours, as indicated by the amount of water collected. The reaction mixture is then charged into a stainless steel hydrogenation container and 5 percent palladium-on-carbon is added to the mixture. The solution is then hydrogenated under a hydrogen pressure of between about 25 and 200 psi. at a temperature between about 35° and 55° C. Following the completion of the reduction as indicated by the amount of hydrogen absorbed, the catalyst is filtered and the filtrate is saturated with anhydrous hydrogen chloride. The reaction product, the methoxylated secondary amine, is precipitated as the hydrochloride salt.

The compounds of the invention wherein R is hydrogen and $R_1$ is methyl are prepared by the reductive alkylation of 3,4-dimethoxyphenylethyl amine with the desired mono- or dimethoxylated phenyl butane-3-one (n=2) or the mono- or dimethoxylated phenylacetone (n=1). The reductive alkylation is carried out according to the reductive alkylation procedures described above for the preparation of the compounds wherein R is methyl. In an alternative procedure, the compounds of the above formula wherein R is hydrogen and $R_2$ is methyl are prepared by the condensation of 3,4-dimethoxyphenylacetic acid with a methoxylated 1-phenyl-3-aminobutane (n=2) or with a methoxylated 1-phenyl-2-aminopropane (n=1) to form as an intermediate the methoxylated amide. According to this procedure, the amine and the acid are condensed to form the amide by stirring a mixture of the two compounds at a temperature of about 200°C. The amide reaction product thus obtained is then reduced under nitrogen with borane to provide the secondary amine. The borane reduction is carried out by the addition of a solution of borane in tetrahydrofuran containing an excess of borane to a solution of the methoxylated amide in tetrahydrofuran. The reaction is initially carried out at a temperature between about 0 and 5° C. The reaction mixture is maintained at the reaction temperature for about 3 hours, and thereafter is heated at the reflux temperature for about 4 hours. The reduction product, the methoxylated secondary amine is isolated as the hydrochloride salt in the following manner. The reduction mixture is generally cooled in an ice bath and 3N hydrochloric acid is added to the solution. The acidified reaction mixture is then evaporated to yield the hydrochloride salt of the reduction product as a residue. The residue is recrystallized to obtain the purified methoxylated secondary amine hydrochloride salt.

The methyl ether precursors of the compounds of the Formula I wherein R and $R_1$ are both hydrogen are prepared by the alkylation of 3,4-dimethoxyphenylethylamine with a methoxylated phenyl-n-propyl bromide (n=2) or with a methoxylated phenylethyl bromide (n=1). The alkylation is carried out by heating a mixture of the amine and the bromide at steam bath temperature for about 8 to 18 hours. The amine is employed in excess and in general a 4 to 5 molar excess is used. The secondary amine reaction product is isolated by treating the reaction product mixture with alkali and extracting the basic amines into ether. The ether and excess primary amine are distilled off in vacuo and the secondary amine product is recovered from the crude residue as the hydrochloride salt which is further purified by recrystallization from ethanolether.

The methoxylated secondary amine intermediates prepared as described above are converted to the phenolic secondary amine compounds of the invention by reacting the methoxy secondary amines as the hydrochloride salts or as the free amines with 48 percent hydrobromic acid. The ether cleavage reaction is carried out by dissolving the methoxylated secondary amine as the free base or as a hydrochloride salt in glacial acetic acid containing excess 48 percent hydrobromic acid. The reaction mixture is then heated at the reflux temperature for about 3 to about 6 hours. The reaction mixture is evaporated in vacuo to remove volatile acids and to obtain the reduction product mixture as a crude residue. The residue is recrystallized to obtain the phenolic secondary amine as the hydrobromide salt.

The hydrobromide salt thus obtained can be converted to the free amine according to conventional procedures and the free amine in turn can be converted to the desired salt, for example, the hydrochloride salt or the sulfate salt.

A particularly useful method for the preparation of the compound of the above formulae, wherein R is H, $R_1$ is methyl, $R_2$ is hydrogen and $R_3$ is hydroxy, namely, 3,4-dihydroxy-N-[3-(4-hydroxyphenyl)-1-methyl-n-propyl]-β-phenethylamine, is by the reaction of 4-methoxyphenyl propenyl ketone with 3,4-dimethoxyphenethylamine, followed by the reduction of the amino ketone intermediate to the methoxylated secondary amine. The secondary amine is then reacted with 48 percent hydrobromic acid as described above to provide the compound of the invention. The preparation of the intermediate amino ketone is carried out by the dropwise addition of the propenyl ketone to a solution of homoveratrylamine in toluene. The addition is carried out at a temperature of about 0° to −5° C. The reaction mixture is then allowed to stand at room temperature for approximately two days. Thereafter, the reaction mixture is cooled in an ice-water bath and is acidified with 1N hydrochloric acid. The reaction product 3-(3,4-dimethoxyphenethylamino)-1-(4-methoxyphenyl)butane-1-one precipitates from the reaction mixture as the hydrochloride salt. The amino ketone hydrochloride is then catalytically reduced to provide the trimethylether secondary amine. The hydrogenation is carried out by dissolving the amino ketone hydrochloride in ethanol containing sulfuric acid. Five percent palladium-on-carbon is added to the solution and the solution is hydrogenated under a hydrogen pressure of about 50 psi. The reduction is allowed to proceed at a temperature of about 60° C. until the calculated amount of hydrogen has been absorbed. The hydrogenolysis product is isolated by filtering the catalyst and evaporating the filtrate in vacuo to yield the reduction product mixture as a residual solid. The residue is crystallized, preferably from methanol, to yield the purified product, 3,4-dimethoxy-N-[3-(4-methoxyphenyl)-1-methyl-n-propyl]-β-phenethylamine hydrochloride.

The foregoing procedures for the preparation of the compounds of the invention are illustrated in more detail in the examples provided hereinafter.

Some of the compounds provided by this invention possess a center of asymmetry. Each of the methods described above for the preparation of these compounds provides the dl-racemates thereof. The asymmetric compounds can be resolved into their respective, optically active, d- and l- isomers. Whereas the compounds of the invention can be resolved directly, it is preferable to resolve the intermediate methoxylated secondary amines and thereafter subject the resolved d- and l- isomers to methoxyl cleavage with 48 percent hydrobromic acid. Particularly useful resolving agents for the methoxylated secondary amines are the dibenzoyl-d- and l-tartaric acids. For example, dl-3,4-dimethoxy-N-[3-(4-methoxyphenyl)-1-methyl-n-propyl]-phenethylamine is dissolved in benzene and the solution is mixed with a solution of the resolving agent, dibenzoyl-d-tartaric acid, in benzene. The resolution mixture is allowed to stand overnight at about room temperature during which time a crystalline precipitate of the salt of the d-amine d-acid forms. The salt is purified by repeated recrystallization from 95 percent ethanol until a constant melting point is obtained. The free d-amine is obtained from the salt by dissolving the salt in water and forming the free amine by the addition of a suitable base such as 5 percent sodium hydroxide. The free base is then extracted from the aqueous alkaline mixture. The extract is dried and is evaporated to yield the d-amine, d-3,4-dimethoxy-N-[3-(4-methoxyphenyl)-1-methyl-n-propyl]phenethylamine.

The original mother liquor, containing in solution the salt of the l-amine d-acid, is evaporated in vacuo, and the residue is dissolved in water. The aqueous solution is made basic by the addition of 5 percent sodium hydroxide. The l-amine comes out of the solution as an oil and is extracted with diethyl ether. The ether extract is dried, and thereafter is evaporated in dryness to obtain the l-amine as an oily residue. The l-amine is dissolved in benzene and the solution is mixed with a benzene solution of dibenzoyl-l-tartaric acid to provide a crystalline precipitate of the l-amine l-acid salt. The salt is filtered and repeatedly recrystallized from a suitable solvent such as 95 percent ethanol until a constant melting point is achieved. Thereafter, the l-amine is obtained by following procedures similar to those employed for the preparation of the d-amine as described above.

The resolved d- and l-amines are then individually reacted with 48 percent hydrobromic acid according to the procedures described above to obtain the d- and l-phenolic amines.

The resolved compounds of the invention can be converted to the desired acid addition salts with pharmaceutically acceptable mineral acids, such as, hydrochloric acid, hydrobromic acid, phosphoric acid and sulfuric acid. The preferred pharmaceutically acceptable salts are the hydrochlorides and the hydrobromides.

The hydroxyalkyl dopamine derivatives useful in the present method are administered by intravenous infusion in the form of a salt as the hydrochloride or hydrobromide salt. Preparations of the salt suitable for intravenous infusion are, for example, a 5% glucose solution containing a desirable clinical concentration of the compound in the salt form. Such solution is desirably maintained at an acid pH.

The compound is administered at the aforementioned rate of between 0.5 to 10 mcg./kg./min. until the contractile force of the heart muscle is restored. As the host responds the rate of infusion may be decreased or discontinued altogether. In certain instances a particular host may require continuous administration for long durations; for example, a few days, while with other hosts a single infusion of a short duration may suffice to produce the desired restoration of contractility.

The compounds of this invention are relatively non-toxic substances with a high therapeutic index. For example, dl-3,4-dihydroxy-N-[3-(4-hydroxyphenyl)-n-propyl]-α-methyl-β-phenethylamine hydrobromide has an $LD_{50}$ in mice of $82.73 \pm 5.72$ mg./kg. and dl-3,4-dihydroxy-N-[3-(4-hydroxyphenyl)-1-methyl-n-propyl]-phenethylamine hydrochloride has an $LD_{50}$ of $73.19 \pm 3.68$ mg./kg.

As previously mentioned, it is well known that when an asymmetric center exists in a drug, the resolution of the racemic mixture may yield optical antipodes with differing pharmacological activities. An example of this in the instant case is provided by the resolution of dl-3,4-dihydroxy-N-[3-(4-hydroxyphenyl)-1-n-propyl]-phenethylamine.

The following Table I shows the inotropic activity for the dl-racemate and the d- and l-resolved isomers thereof.

Table I

Cardiac and Blood Pressure Effects of dl-, d- and l-3,4-dihydroxy-N-[3-(4-hydroxyphenyl)-1-methyl-n-propyl]-β-phenethylamine in dogs.

| Compound | Contractile Potency mcg./kg./min. i v. | | Heart Rate Increase Beats/minute at Effective dose | | Blood Pressure Change mm. Hg. at Effective dose | |
|---|---|---|---|---|---|---|
| | $ED_{50}$ | $ED_{100}$ | $ED_{50}$ | $ED_{100}$ | $ED_{50}$ | $ED_{100}$ |
| dl- | $3 \pm 1$ | $10 \pm 3$ | $13 \pm 4$ | $30 \pm 4$ | $3 \pm 5$ | $6 \pm 6$ |
| d- | $2.8 \pm .3$ | $6.1 \pm .4$ | $11 \pm 3$ | $28 \pm 7$ | $8 \pm 2$ | $6 \pm 3$ |
| l- | $9 \pm 2$ | $25 \pm 5$ | $8 \pm 5$ | $28 \pm 9$ | $39 \pm 3$ | $63 \pm 4$ |

Although, as indicated by the data in the above Table, the 1-isomer is somewhat less active than either the d-isomer or dl-racemate on contractile force, its marked pressor activity makes it especially useful in the treatment of acutely depressed cardiac contractility complicated by marked hypotension.

The following examples more fully illustrate the present invention.

EXAMPLE 1

Preparation of 3,4-dihydroxy-N-[3-(4-hydroxyphenyl)-1-methyl-n-propyl]-β-phenethylamine.

In a stainless steel hydrogenation bottle were placed 17.6 g. (0.1 mole) of 4-(p-methoxyphenyl)-3-buten-2-one, 80 ml. of ethyl acetate, and 1 g. of Raney nickel catalyst. The hydrogenation bottle was attached to a Paar low pressure hydrogenation apparatus and the solution was hydrogenated under an initial hydrogen pressure of 50 psi. The hydrogenation was carried out at room temperature and after about 12 hours one equivalent of hydrogen had been absorbed. The catalyst was filtered from the reduction mixture and 18.1 g. (0.1 mole) of homoveratrylamine were added to the reduction mixture. To the reduction mixture was then added 3.5 g. of 5 percent palladium on carbon catalyst and the mixture was hydrogenated under a hydrogen pressure of 50 psi. at room temperature for 12 hours. The catalyst was removed by filtration and the filtrate was evaporated to a small volume. The concentrated filtrate was dissolved in diethyl ether and the ethereal solution was saturated with anhydrous hydrogen chloride. The reduction product, 3,4-dimethoxy-N-[3-(4-methoxyphenyl)-1-methyl-n-propyl]phenethylamine was precipitated as the hydrochloride salt. The salt was filtered and recrystallized from ethanol melting at about 147°–149° C.

Elemental analysis calculated for $C_{21}H_{30}NO_3Cl$:
Theory: C, 66.39; H, 7.96; N, 3.69.
Found: C, 66.36; H, 8.07; N, 3.78.

To a solution of 101.2 g. of the trimethoxy secondary amine, obtained as described above, in 3060 ml. of glacial acetic acid was added 1225 ml. of 48 percent hydrobromic acid and the reaction mixture heated at the reflux temperature for 4 hours. The reaction mixture was then cooled and evaporated to a small volume. The crystalline residue which formed was filtered and dried in vacuo. The dried crystalline residue was then triturated with ethyl acetate and redried to yield 97.3 g. of crude crystalline material. The crude product was dissolved in 970 ml. of warm water to obtain a yellow solution. To the solution was added successively by dropwise addition 75 ml. of 1 N and 75 ml. of 2 N hydrochloric acid. Following the dropwise addition, the solution was allowed to stir with ice cooling. The impurities which precipitated were removed by filtration through a gauze filter. Concentrated hydrochloric acid was then added dropwise. When approximately 50 to 75 ml. of the concentrated acid had been added with ice bath cooling a pale yellow oil precipitated along with a white solid precipitate. With continued stirring of the cold solution, the pale yellow oil crystallized. The cold solution was then allowed to stand overnight and all crystalline material filtered through a sintered glass filter. The filtrate was treated with an additional 300 ml. of concentrated hydrochloric acid to yield a heavy white precipitate. The precipitate was filtered, dried and combined with the initial precipitate obtained as described above. The combined precipitated product, 3,4-dihydroxy-N-[3-(4-hydroxyphenyl)-1-methyl-n-propyl]-β-phenethylamine hydrochloride, had a melting point of about 184°–186° C. after recrystallization from boiling 4N hydrochloric acid.

Elemental analysis calculated for $C_{18}H_{24}ClNO_3$.
Theory: C, 63.99; H, 7.16; N, 4.15; Cl, 10.49
Found: C, 63.79; H, 7.06; N, 4.42; Cl, 10.55.

EXAMPLE 2

In a round bottom three necked flask equipped with a reflux condenser, a stirrer and a Dean-Starke water separator was placed 100 g. of 1-(4-methoxyphenyl)-3-butanone, 1 g. of p-toluenesulfonic acid, 110 g. of homoveratrylamine and 400 ml. of toluene. The solution which was obtained was heated at the reflux temperature for 3 hours. During this time the theoretical yield of water was collected in the water trap. The reaction mixture was then allowed to stir overnight. The reaction mixture was charged into a stainless steel hydrogenation bottle and 20 g. of 5 percent palladium on carbon catalyst were added. The reaction mixture was hydrogenated at a temperature of about 50° C. under a hydrogen pressure of 50 psi. The reduction was allowed to continue for 16 hours during which time the theoretical uptake of hydrogen was observed. The catalyst was filtered and anhydrous hydrogen chloride was passed through the filtrate until the saturation point was achieved. The acidified filtrate was then cooled and the reduction product began to precipitate as the hydrochloride salt. The addition of ether to the acidified filtrate facilitated the precipitation of the product. The crystalline precipitate was filtered to yield 148.3 g. of the reduction product, dl-3,4-dimethoxy-N-[3-(4-methoxyphenyl)-1-methyl-n-propyl]-β-phenethylamine hydrochloride.

EXAMPLE 3

A mixture of 143.4 g. of 3-(4-methoxyphenyl)-1-methyl-n-propylamine and 157.0 g. of 3,4-dimethoxyphenylacetic acid was stirred and heated at a temperature of 200° C. Heating was continued at this temperature for 4 hours and the dark solution obtained was poured into a beaker and allowed to cool. The cooled reaction product mixture was dissolved in 3.1 of ethyl acetate and the solution was washed consecutively with one liter of water, one liter of 1N hydrochloric acid, 1 liter of water, 1 liter of 1N sodium hydroxide and finally with 1 liter of a saturated solution of sodium chloride. The ethyl acetate solution of the reaction product was then dried and evaporated to a small volume. The concentrate was dissolved in Skellysolve-B and on cooling, 236.2 g. of the reaction product, 2-(3,4-dimethoxyphenyl)-N-(4-methoxyphenyl-1-methyl-n-propyl)acetamide, was obtained as a crystalline solid melting at about 93° to 95° C.

A solution of 232.5 g. of the amide prepared as described above in one liter of tetrahydrofuran was added under nitrogen by dropwise addition with stirring to a one molar solution of borane in 1.3 liters of cold tetrahydrofuran. The reaction and the addition was carried out at a temperature between about 0° to −5° C. The addition required approximately 3 hours. When addition was complete the reaction solution was then heated at the reflux temperature for 4 hours. Thereafter the reaction mixture was cooled to room temperature and allowed to stand overnight. The reaction mixture was then cooled in an ice bath to 10° C. and 420 ml. of 3N hydrochloric acid were added dropwise to the solution. The acidified solution was evaporated to yield a gummy residue. The gummy residue was taken up in a minimum amount of ethanol and the ethanol solution was diluted with diethyl ether with cooling.

The precipitate which formed was filtered and was washed with ethyl acetate and then with diethyl ether. The precipitated product, dl-3,4-dimethoxy-N-[3-(4-methoxyphenyl)-1-methyl-n-propyl]-β-phenethylamine hydrochloride was recrystallized from ethanol to yield 103.0 g. melting at about 148°–150° C.

EXAMPLE 4

Into a round bottom three-necked flask equipped with a stirrer, a reflux condenser, and a dropping funnel were placed 583 g. of anisole, 720 g. of aluminum chloride, and 2.37 liters of carbon disulfide. The reaction solution was stirred and 565 g. of crotonyl chloride were added by dropwise addition at such a rate as to maintain a continuous reflux. As the reaction mixture thickened, an additional 2.37 liters of carbon disulfide were added. The resulting reaction mixture which had the consistency of a slurry was refluxed for 4 hours and thereafter was poured into a mixture of 9 kg. of ice, 2 liters of water and 900 ml. of concentrated hydrochloric acid. The carbon disulfide was removed from the dilute acidified reaction mixture under vacuum. The aqueous residue was then extensively extracted with dichloromethane. The extract was washed with water and dried and was then evaporated in vacuo to yield the condensation product, p-methoxyphenyl propenyl ketone as an oil having a boiling point of about 135° C. (0.5 mm).

To a solution of 90 g. of homoveratrylamine in 300 ml. of toluene maintained at a temperature of −5° C. were added by dropwise addition 88 g. of p-methoxyphenyl propenyl ketone. The reaction mixture was then allowed to stand at room temperature for about 3 days. The mixture was then cooled in an ice water bath and three, 100 ml. portions of 1 N hydrochloric acid were added. The reaction product, 158 g. of 3-(3,4-dimethoxyphenylethylamino)-1-(4-methoxyphenyl)-butane-1-one, precipitated as the hydrochloride salt. The crystalline hydrochloride salt was recrystallized from a mixture of methanol and ethyl acetate.

Elemental analysis calculated for $C_{21}H_{29}ClNO_4$.
Theory: C, 63.87; H, 7.40; Cl, 8.98; N, 3.55; O, 16.20.
Found: C, 63.76; H, 7.67; Cl, 9.25; N, 3.53; O, 16.44.

A solution of 39.3 g. of the amino ketone thus obtained in 700 ml. of ethanol containing 3.5 ml. of concentrated sulfuric acid and 10 g. of 5 percent palladium carbon catalyst was hydrogenated in a stainless steel bottle under an initial hydrogen pressure of 50 psi. The hydrogenation was carried out at a temperature of 60° C. for 2 hours during which time 2 equivalents of hydrogen were absorbed. The catalyst was filtered and the filtrate evaporated in vacuo and the residue dissolved in ethanol. The ethanol solution was filtered and the filtrate was concentrated in vacuo. Water was added to the concentrate and the aqueous solution was made basic with potassium carbonate and extracted with ether. The extract was dried and then saturated with anhydrous hydrogen chloride to precipitate 32 g. of crystalline product dl-3,4-dimethoxy-N-[3-(4-methoxyphenyl)-1-methyl-n-propyl]-β-phenethylamine hydrochloride melting at about 147° C.

EXAMPLE 5

Preparation of 3,4-Dihydroxy-N-[3-(4-hydroxyphenyl)-n-propyl]-α-methyl-β-phenethylamine.

A mixture of 277.2 g. of β-(p-methoxyphenyl)propionic acid and 355.3 g. of α-methylhomoveratrylamine was stirred and heated at a temperature of 200° C. for 4 hours. The reaction mixture was cooled to room temperature and dissolved in ethyl acetate. The solution was then washed successively with water, dilute hydrochloric acid, water, 1N sodium hydroxide and a saturated sodium chloride solution. The washed solution was dried and evaporated to a small volume. The concentrate was cooled and diluted with Skellysolve B to provide 496 g. of 3-(4-methoxyphenyl)-N-(3,4-dimethoxy-α-methyl-β-phenethyl)-propionamide melting at about 99°–101° C.

Elemental analysis calculated for $C_{21}H_{27}NO_4$:
Theory: C, 70.56; H, 7.61; N, 3.92.
Found: C, 69.69; H, 7.76; N, 3.93.

A solution of 500 g. of the amide in 2.5 l. of anhydrous tetrahydrofuran was added dropwise under nitrogen to 3 l. of a one molar solution of borane in tetrahydrofuran. The addition was carried out at 0° C. over 2.5 hours. With stirring the reaction mixture was gradually heated to the reflux temperature. The reaction mixture was heated at the reflux temperature for 3 hours and was then allowed to stand overnight at room temperature. The mixture was cooled in an ice bath and 900 ml. of 3N hydrochloric acid were slowly added. The acidified mixture was evaporated to a concentrate and 290.7 g. of crude 3,4-dimethoxy-N-[3-(4-methoxyphenyl)-n-propyl]-α-methyl-β-phenethylamine hydrochloride formed as a precipitate. The product was purified by recrystallization from ethanol.

Elemental analysis calculated for $C_{21}H_{30}ClNO_3$:
Theory: C, 66.39; H, 7.96; N, 3.69, Cl, 9.33.
Found: C, 66.56; H, 8.21; N, 3.79; Cl, 3.79.

A solution of 50 g. of the above amine hydrochloride in 750 ml. of glacial acetic acid and 300 ml. of 48% hydrobromic acid was heated at the reflux temperature for four hours. The reaction mixture was then evaporated under vacuum and the residue was dissolved in a 4 to 1 mixture of ethanolbenzene. The solution was evaporated to dryness in order to remove volatile acids. The dissolution in ethanol-benzene followed by evaporation was repeated three times to provide the crude reaction product substantially free of acids. The crude residue was crystallized from ethyl acetate to yield 39 g. of 3,4-dihydroxy-N-[3-(4-hydroxyphenyl)-n-propyl]-α-methyl-β-phenethylamine hydrobromide melting at about 163°–168° C.

EXAMPLE 6

Preparation of 3,4-Dihydroxy-N-[3-(3-hydroxyphenyl)-n-propyl]-β-phenethylamine.

A mixture of 50 g. of 3,4-dimethoxyphenethylamine and 15 g. of 3-(3-methoxyphenyl)-n-propyl bromide was heated overnight at steam bath temperature. While still warm, the reaction mixture was poured into a 10% sodium hydroxide solution with stirring. The alkaline mixture was extracted twice with ether and the extracts were combined and washed with water and dried. The dried extract was evaporated to yield a partially crystalline residue. Unreacted primary amine was distilled from the residue in vacuo (0.3 mm) and the remaining residue dissolved in ether. The ether solution was saturated with hydrogen chloride to precipitate 3,4-dimethoxy-N-[3-(3-methoxyphenyl)-n-propyl]-β-phenethylamine hydrochloride. The salt was recrystallized once from acetone-ether and three times from ethanol-ether to yield 12 g. of the purified salt melting at about 117° to 124° C. The nuclear magnetic resonance spectrum of the hydrochloride salt was consistent with the structure of the reaction product.

The reaction product, 12 g., was dissolved in a mixture of 175 ml. of 48% hydrobromic acid and 470 ml. of glacial acetic acid and the solution was heated at the reflux temperature for 3 hours. The reaction mixture was cooled to room temperature and evaporated in a rotary evaporator. The residue was dried with ethanol/benzene (80:20) and the solvents decanted from the oily residue. The residue was dissolved in ethyl acetate and the solution was extracted once with 40 ml. of water and once with 20 ml. of water. The brown aqueous extracts were combined and titrated successively by dropwise addition with 30 ml. of 1N hydrochloric acid and with 30 ml. of 2N hydrochloric acid. A brown oil precipitated and the mother liquor was decanted. With stirring, 18 ml. of concentrated hydrochloric acid was added to the mother liquor and the reaction product, 3,4-dihydroxy-N-[3-(3-hydroxyphenyl)-n-propyl]-β-phenethylamine hydrochloride formed as a light yellow oil. The mixture was refrigerated and the supernatant decanted from the product. The product was dissolved in ethanol and the solution evaporated to dryness. The residual product, as a yellow oil, was repeatedly flushed with a mixture of alcohol and benzene, thoroughly dried, and then crystallized from acetone melting at about 142°–144° C. The nuclear magnetic resonance spectrum of the crystalline material was consistent with the structure of the product.

EXAMPLE 7

Preparation of 3,4-dihydroxy-N-[3-(3,4-dihydroxyphenyl)-n-propyl)-β-phenethylamine.

3,4-Dimethoxyphenethylamine was reacted with β-(3,4-dimethoxyphenyl)propionic acid and the reaction product N-(3,4-dimethoxyphenylethyl)-3,4-dimethoxyphenylpropionamide was reduced under nitrogen with borane in anhydrous tetrahydrofuran. The secondary amine reduction product, 3,4-dimethoxy-N-[3-(3,4-dimethoxyphenyl)-n-propyl]-β-phenethylamine was reacted with 48% hydrobromic acid in glacial acetic acid by heating at the reflux temperature for three hours to provide 3,4-dihydroxy-N-[3-(3,4-dihydroxyphenyl)-n-propyl]-β-phenethylamine hydrobromide melting at about 176°–178° C.

Elemental analysis calculated for $C_{17}H_{22}BrNO_4$
Theory: C, 53.14; H, 5.77; N, 3.65.
Found: C, 52.96; H, 5.56; N, 3.42.

EXAMPLE 8

Preparation of 3,4-Dihydroxy-N-[2-(3,4-dihydroxyphenyl)ethyl]-β-phenethylamine.

A mixture of 100 g. of 3,4-dimethoxyphenethylamine and 20 g. of 3,4-dimethoxyphenethyl bromide was heated at steam bath temperature overnight. The reaction mixture was poured into a 10% solution of sodium hydroxide and the alkaline mixture extracted with ether. The extract was dried and evaporated and the unreacted primary amine distilled from the residue under vacuum. The residue was slurried in a mixture of dilute hydrochloric acid and ether. The crystalline precipitate of the hydrochloride salt of the reaction product which formed was filtered from the mixture. The ether phase was washed with water and discarded and the wash combined with the aqueous acid phase. The aqueous acid phase was basified with 50% sodium hydroxide and the oily reaction product extracted with ether. The extract was washed with water until neutral and then was dried over magnesium sulfate. The dried extract was saturated with hydrogen chloride to precipitate the reaction product as the hydrochloride salt. This precipitate was combined with the crystalline salt obtained above and the whole triturated with acetone and filtered. The salt was recrystallized from ethanol-ether to yield the purified product, di-(3,4-dimethoxyphenethyl)amine hydrochloride melting at about 202° to 204° C.

Elemental analysis calculated for $C_{20}H_{28}ClNO_4$:
Theory: C, 62.89; H, 7.39; N, 3.66.
Found: C, 62.68; H, 7.57; N, 3.71.

The secondary amine hydrochloride was reacted with 48% hydrobromic acid in glacial acetic acid according to the procedure described in preceding Examples to yield di-(3,4-dihydroxyphenylethyl)amine hydrobromide. The salt was purified by repeated crystallization from ethanol-ether and melted at about 121°–127° C. with decomposition.

Elemental analysis calculated for $C_{16}H_{20}BrNO_4$:
Theory: C, 51.90; H, 5.44; N, 3.78.
Found: C. 51.71; H. 6.25; N, 4.14.

EXAMPLE 9

Resolution of 3,4-dimethoxy-N-[3-(4-methoxyphenyl)-1-methyl-n-propyl]-β-phenethylamine.

To a solution of 448 g. (1.19 mole) of dibenzoyl-d-tartaric acid monohydrate in 500 ml. of hot 90% ethanol was added 409.8 g. (1.19 mole) of 3,4-dimethoxy-N-[3-(4-methoxyphenyl)-1-methyl-n-propyl]-β-phenethylamine. On cooling a crystalline precipitate of the d-amine d acid salt formed. The salt was filtered and washed twice with 1500 ml. portions of ethyl acetate before drying to yield 245.8 g. melting at about 169°–171° C.

The mother liquor of the above precipitation was evaporated to dryness and the residue suspended in a mixture of water and ethanol. The suspension was made strongly basic by the addition of sodium hydroxide and the free amine which formed was extracted with ether. The extract was dried over sodium sulfate and evaporated to dryness to yield 236.4 g. of free secondary amine.

The whole amount of the free amine was added to a solution of 258 g. of dibenzoyl-l-tartaric acid monohydrate in 3 l. of 90% ethanol. The crystalline salt of the l-amine l-acid formed as a precipitate and was filtered. The material was recrystallized six times from approximately 11 liters of alcohol to yield 189.5 g. melting at about 177° C.

The l-3,4-dimethoxy-N-[3-(4-methoxyphenyl)-1-methyl-n-propyl]-β-phenethylamine dibenzoyl-l-tartaric acid salt prepared as described above was dissolved in a mixture of water and ethanol and the solution was made strongly basic by the addition of sodium hydroxide. The free l-amine was extracted with ether, and the extract was dried and evaporated to yield 121.3 g. of the free amine.

The free amine was dissolved in a mixture of 1455 ml. of 48% hydrobromic acid and 3639 ml. of glacial acetic acid and the mixture was heated at the reflux temperature for 5 hours. The reaction mixture was evaporated to dryness in vacuo and the residue was washed four times with ethanol-benzene before drying to yield l-3,4-dihydroxy-N-[3-(4-hydroxyphenyl)-1-methyl-n-propyl]-β-phenethylamine hydrobromide.

The phenolic amine as the hydrobromide salt was purified and converted to the hydrochloride salt by recrystallization from boiling 4N hydrochloric acid. The hydrobromide salt was dissolved in boiling 4N hydrochloric acid and charcoal was added to the solution. After stirring the charcoal was filtered and the hot filtrate was reheated to the boiling point to redissolve the precipitated salt. On cooling there was obtained 123.5 g. of l-3,4-dihydroxy-N-[3-(4-hydroxyphenyl)-1-methyl-n-propyl]-β-phenethylamine hydrochloride melting at 197°–198° C. after drying.

Elemental analysis calculated for $C_{18}H_{23}NO_3 \cdot HCl$
Theory: C, 63.99; H, 7.16; N, 4.15; Cl, 10.49.
Found: C, 63.69; H, 7.12; N, 4.09; Cl, 10.55.
Specific rotation: $[\alpha]_{365}^{30} - 39.4$ (C=8.8154 mg. per 1. of methanol).

The d-amine d-acid salt obtained as described above was converted to the methoxy d-amine with base according to the procedure previously described for the l isomer. The free amine was dissolved in ether and converted to the hydrochloride with hydrogen chloride. The hydrochloride salt was filtered and recrystallized four times from ethanol ether to obtain the purified d-3,4-dimethoxy-N-[3-(4-methoxyphenyl)-1-methyl-n-propyl]-β-phenethylamine hydrochloride melting at about 147°–148° C.

Elemental analysis for $C_{21}H_{29}NO_3 \cdot HCl$:
Theory: C, 66.39; H, 7.96; N, 3.69.
Found: C, 66.52; H, 7.70; N, 3.84.

The d-methoxy amine was converted to the phenolic amine with hydrobromic acid in glacial acetic acid and was obtained as the purified hydrochloride salt by recrystallization from boiling 4N hydrochloric acid according to the procedures described above for the l-isomer. The crystalline hydrochloride salt of the d-isomer thus obtained melted at about 197°–198° C. and had a specific rotation of $[\alpha]_{365}^{30}+38.4$.

EXAMPLE 10

Preparation of 3,4-Dihydroxy-N-[2-(3-hydroxyphenyl)-1-methylethyl]-α-methyl-β-phenethylamine.

A solution of 29.2 g. (0.15 mole) of 3,4-dimethoxyphenyl-iso-propylamine and 24.6 g. (0.15 mole) of 3-methoxyphenylacetone in one liter of benzene containing one gram of p-toluenesulfonic acid was heated at the reflux temperature in a round bottomed flask equipped with a Dean-Stark water trap. When the theoretical amount of water was collected the reaction mixture was evaporated to dryness. The residue was dissolved in 250 ml. of ethanol and 5% palladium on carbon catalyst was added to the solution. The mixture containing the methoxylated imine was hydrogenated at a temperature of 50° C. for 5 hours. The catalyst was filtered and the filtrate evaporated to dryness. The residue was dissolved in ether and the solution saturated with hydrogen chloride. Upon the addition of dry acetone to the ethereal solution the hydrochloride 3,4-dimethoxy-N-[2-(3-methoxyphenyl)-1-methylethyl]-α-methyl-β-phenethylamine precipitated. The salt was filtered and triturated with dry acetone. The salt melted at about 161° to 163° C. after two recrystallizations from ethanol-ether.

Elemental analysis for $C_{21}H_{29}NO_3 \cdot HCl$:
Theory: C, 66.39; H, 7.96; N, 3.69.
Found: C, 66.46; H, 7.95; N, 3.98.

The methoxylated amine hydrochloride thus prepared was dissolved in a mixture of 420 ml. of glacial acetic acid and 168 ml. of 48% hydrobromic acid and the solution was heated at the reflux temperature for 4 hours. The mixture was evaporated to dryness and the residue was washed with ethanolbenzene. The residue was then dissolved in water and the solution with ethyl acetate. To the aqueous solution was added 70 ml. of 12% hydrobromic acid to form a white precipitate. The precipitate was filtered and to the filtrate were successively added 5 ml. portions of 24% and 36% hydrobromic acid followed by 25 ml. of 48% hydrobromic acid. On refrigeration a pink oil formed. Another 25 ml. portion of 48% hydrobromic acid was added and with seeding the oil crystallized. The precipitates were combined and recrystallized from ethanol-ether to yield 3,4-dihydroxy-N-[2-(3-hydroxyphenyl)-1-methylethyl]-α-methyl-β-phenethylamine hydrobromide melting at about 116° C.

Elemental analysis for $C_{18}H_{23}NO_3 \cdot HBr$:
Theory: C, 56.55; H, 6.33; N, 3.66.
Found: C, 56.33; H, 6.39; N, 3.48.

We claim:

1. The method for increasing cardiac contractility in a warm-blooded animal suffering from acutely depressed cardiac contractility which comprises administering to said animal at a rate of between 0.5 and 10 micrograms per kilogram of body weight per minute a compound of the formula

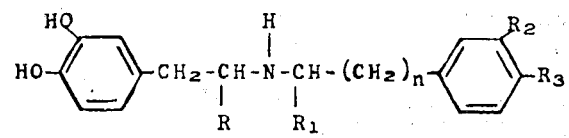

wherein
R and $R_1$ are hydrogen or methyl;
$R_2$ and $R_3$ are hydrogen or hydroxy, at least one of $R_2$ and $R_3$ being hydroxy;
n is 1 or 2;
subject to the limitation that when n is 2, $R_2$ is hydrogen and $R_3$ is hydroxy, one of R or $R_1$ is hydrogen and the other is methyl; and the pharmaceutically acceptable acid addition salts thereof with mineral acids.

2. The method of claim 1 wherein the compound administered is a compound of the formula

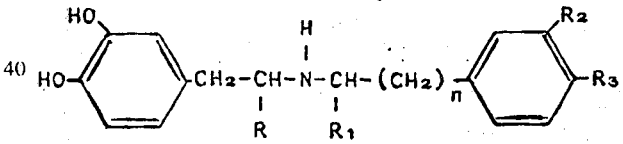

wherein
R and $R_1$ are hydrogen or methyl;
$R_2$ and $R_3$ are hydrogen or hydroxy, at least one of $R_2$ and $R_3$ being hydroxy;
n is 1 or 2;
subject to the limitation that when n is 2, $R_2$ is hydrogen and $R_3$ is hydroxy, one of R or $R_1$ is hydrogen and the other is methyl; with the further limitations that when n is 2 and $R_2$ and $R_3$ are both hydroxy, then $R_1$ is hydrogen, and when n is 1, $R_2$ is hydrogen and $R_3$ is hydroxy, then R and $R_1$ are both hydrogen; and the pharmaceutically acceptable acid addition salts with mineral acids.

3. The method of claim 2 wherein the compound administered is 3,4-dihydroxy-N-[3-(4-hydroxyphenyl)-1-methyl-n-propyl]-β-phenethylamine hydrochloride.

4. The method of claim 2 wherein the compound administered is levo-3,4-dihydroxy-N-[3-(4-hydroxyphenyl)-1-methyl-n-propyl]-β-phenethylamine hydrochloride.

5. The method of claim 2 wherein the compound administered is 3,4-dihydroxy-N-[3-(3-hydroxyphenyl-n-propyl]-β-phenethylamine hydrochloride.

6. The method of claim 2 wherein the compound administered is 3,4-dihydroxy-N-[3-(4-hydroxyphenyl)-n-propyl]-α-methyl-β-phenethylamine hydrochloride.

7. The method of claim 2 wherein the compound administered is 3,4-dihydroxy-N-[2-(3,4-dihydroxyphenyl)ethyl]-β-phenethylamine.

8. The method of claim 2 wherein the compound administered is 3,4-dihydroxy-N-[3-(3,4-dihydroxyphenyl)-n-propyl]-β-phenethylamine hydrochloride.

* * * * *